United States Patent [19]

Wawro et al.

[11] Patent Number: 4,887,154
[45] Date of Patent: Dec. 12, 1989

[54] LAMP ASSEMBLY AND RECEPTACLE

[75] Inventors: Thaddeus J. Wawro, Auburn; Stanley R. English, Elbridge; Dominick Danna, Syracuse, all of N.Y.

[73] Assignee: Welch Allyn, Inc., Skaneateles Falls, N.Y.

[21] Appl. No.: 201,062

[22] Filed: Jun. 1, 1988

[51] Int. Cl.$^4$ .......................... H04N 7/18; A61B 1/06
[52] U.S. Cl. ......................................... 358/98; 358/93; 128/6; 362/294
[58] Field of Search ............... 358/93, 98, 240; 128/6; 362/33, 32, 294

[56] References Cited

U.S. PATENT DOCUMENTS

| | | | |
|---|---|---|---|
| 4,532,918 | 8/1985 | Wheeler | 358/98 |
| 4,539,586 | 9/1985 | Danna et al. | 358/98 |
| 4,547,809 | 10/1985 | Southgate | 358/213.16 |
| 4,708,126 | 11/1987 | Toda et al. | 128/6 |

Primary Examiner—John K. Peng
Attorney, Agent, or Firm—Wall and Roehrig

[57] ABSTRACT

A video system having a video processor mounted to a frame, a viewing probe coupled to the video processor that has an imaging device at its distal end, and an illumination apparatus coupled to the viewing probe. The illumination apparatus includes a lamp assembly containing a light source. The lamp assembly also contains first and second heat sink members thermally coupled to the light source. Each of the heat sink members are electrically conducting and electrically insulated from the other. The first and second heat sink members are electrically coupled to the electrodes respectively of the light source. The illumination apparatus further includes a housing containing an opening configured and dimensioned to permit the insertion of the lamp assembly therein. The illumination apparatus further includes a receptacle disposed within and supported by the housing and having first and second electrical conductors. The illumination apparatus further includes resilient clips, connected to the first and the second heat sink members to the first and second conductors of the receptacle respectively, upon insertion of the lamp assembly into the housing. Therefore, the light source can be actuated upon application of a power supply to the first and second electrical conductors of the receptacle.

14 Claims, 3 Drawing Sheets

LAMP ASSEMBLY AND RECEPTACLE

BACKGROUND OF THE INVENTION

The present invention pertains to the field of art involving installation assemblies for light sources that may be employed in illumination systems such as video-equipped endoscopes or borescopes.

In typical video-equipped endoscope and borescope systems, a high voltage white light source is required to illuminate a target in the object plane of the viewing optics. Generally, the white light generated from the light source is optically coupled to a viewing probe which is configured to transmit the light into a target area. The incident light reflected from the target is received by a viewing head of the probe which causes an image to be focused upon an imaging device within the probe. The imaging device receives the image and converts it into electrical signals to be processed. A more detailed description of such a system is provided in U.S. Pat. Nos. 4,532,918 to Wheeler and 4,539,586 to Danna et al.

The light source employed in typical video-equipped endoscope and borescope systems may be a conventional gas-filled flash lamp which is sometimes referred to as an arc discharge lamp. As is well known in the arts, the flash lamp includes a Quartz envelope that is filled with an inert gas such as xenon. When the lamp is triggered, it produces a high intensity flash of white light to ensure that the image received by the viewing probe accurately reflects the true target colors.

As a consequence of the high intensity operation of this type of lamp, a substantial amount of heat is generated. Proper operation of such lamp requires the use of heat sinks to dispose of the heat energy. In many cases, the heat sinks provide structural support for the lamp itself. The heat sinks may also provide an additional function, in that if properly arranged, they act as electrical conductors for connecting lamp electrodes to a power supply. In such an assembly, the electrical power supply leads are connected to the heat sinks to complete the power supply circuit of the lamp.

In most applications, and in particular, applications directed to video-equipped endoscope and borescope instruments, the lifetime of the lamp is substantially shorter in comparison to the lifetime of the instrument. Therefore, the lamp installation should be designed so that it can be easily replaced without having to dismantle a major portion of the instrument.

Typical lamp installations provide access to the lamp assembly, which may include the lamp itself, and the heat sinks surrounding the lamp. However, the assembly is ordinarily fastened to a support frame by screws or other fasteners. In addition, the electrical leads from the lamp power supply are fastened to the lamp or heat sink electrodes by screws. Such an arrangement frequently requires the use of special tools to remove the lamp assembly and replace it with another. Such a procedure may be a difficult and lengthy task particularly for a non-technical or inexperienced operator of the system. Therefore, expedient replacement of a failed lamp is generally not realized for many applications.

One of these applications involves the use of a video-equipped endoscope by a physician to view the internal body organs or cavity of the patient. Failure of a lamp while the probe is inside a patient's body can lead to extended patient discomfort and even trauma. In addition, failure of the lamp at this time usually results in the examination being aborted and can, under certain conditions, make removal of the probe difficult. Another shortcoming with conventional lamp installations is that the lamp assembly is required to cool down before manual replacement is practical.

A further shortcoming of a conventional lamp installation is that the heat sinks of the lamp assembly are rigidly mounted to the lamp itself. Therefore, thermal expansion of the heat sinks during operation may expose the lamp to physical stresses, contributing to the lamp's failure.

OBJECTS AND SUMMARY OF THE INVENTION

It is therefore an object of this invention to provide a lamp installation that avoids the problems associated with a fixed mounted lamp assembly of the prior art.

It is a more particular object of the present invention to provide a lamp installation configured to achieve expedient replacement of the lamp assembly in a video-equipped endoscope or borescope.

It is yet another object of the present invention to provide a lamp installation for use in an endoscope or borescope which employs a flexible support for the lamp and avoids the imposition of physical stresses thereon when the lamp is placed under a thermal load.

It is yet another object of the present invention to provide a lamp assembly that may be removed from its system installation without having to first attach mounting fasteners and electrical leads.

It is yet a further object of the present invention to provide a lamp assembly with a handle means for manually removing the lamp assembly before cool down.

These and other objects of the present invention are attained by an illumination apparatus that includes, a lamp assembly containing a light source and heat disposing means arranged to support the light source. The light source has first and second electrodes. The heat disposing means has first and second heat sink members, each being electrically conducting and electrically insulated from the other. The first and second heat sink members are electrically coupled to the first and the second electrodes, respectively, of the light source. At least one heat sink member is slidably mounted to the light source electrode it is coupled to. The illumination apparatus further includes a housing means that is dimensioned to allow the insertion of the lamp assembly therein. Disposed within and supported by the housing is a receptacle having first and second electrical conductors. At least one of the conductors is slidably mounted in the housing. The illumination device further includes a plug means connected to the heat sink members for detachably coupling the heat sink members to the conductors of the receptacle upon the insertion of the lamp assembly into the housing, thereby creating an electrical circuit that can be excited upon the application of a power supply to the electrical conductors of the receptacle.

BRIEF DESCRIPTIONS OF THE DRAWINGS

One way of carrying out the invention is described in detail below with reference to drawings which illustrate one specific embodiment, in which.

DETAILED DESCRIPTION OF THE INVENTION

Figure 1:
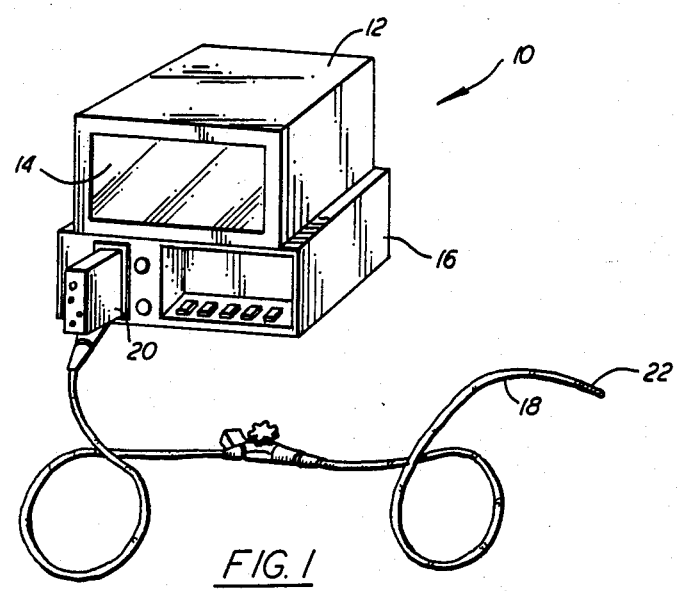
FIG. 1 is a front perspective view of a video endoscopic system embodying the teachings of the present invention.

Referring now to FIG. 1 of the drawings, there is shown a video endoscopic system 10 that is essentially comprised of a video monitor 12 having the usual screen 14, a video processor 16, a viewing probe 18, an interface module 20 that releasably connects the viewing probe to the processor. The viewing probe in an endoscopic system is the portion of the apparatus that enters the body cavity of the patient. At its distal end 22, viewing probe 18 contains a known type of solid state imaging device such as a virtual phase charge coupled imaging device (not shown). A detailed description of video endoscopic system 10 is described in U.S. Pat. Nos. 4,532,918 to Wheeler and 4,539,586 to Danna et al., the contents of which are incorporated herein by reference.

Figure 2:
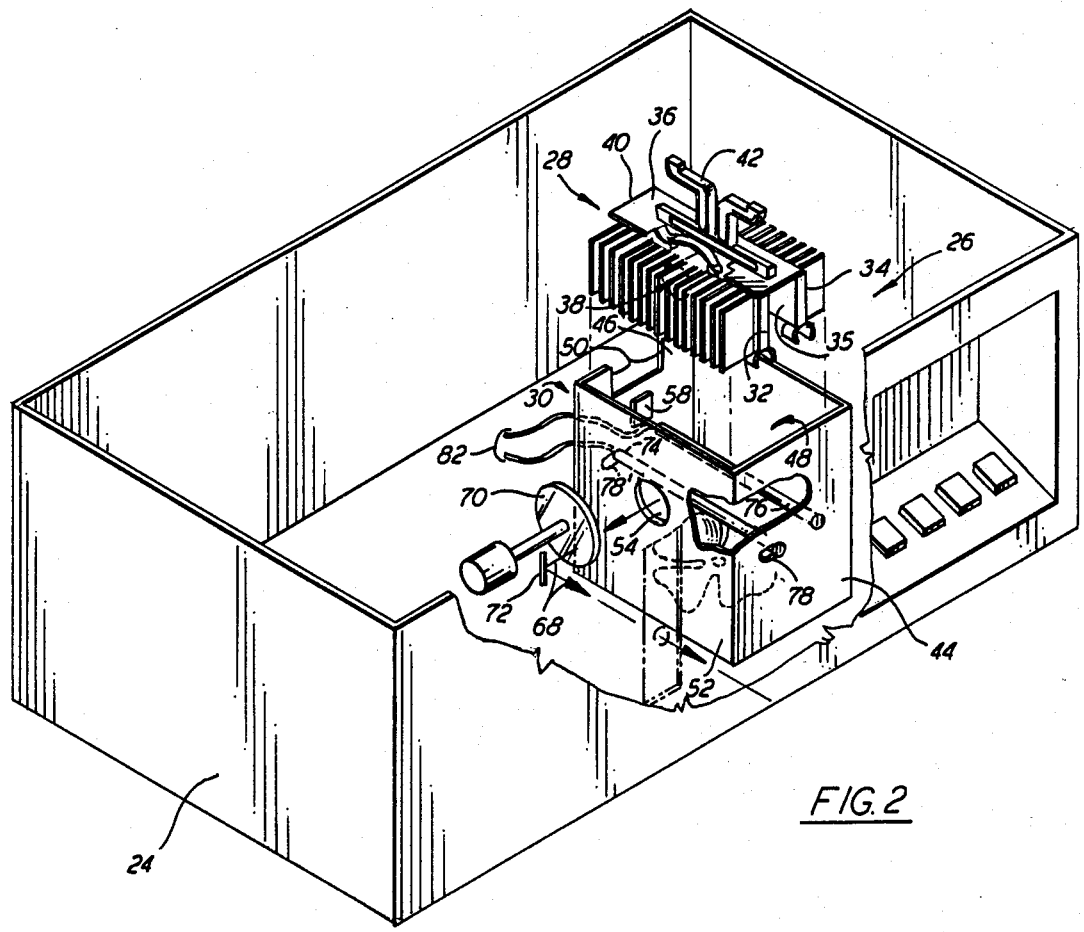
FIG. 2 is an enlarged top perspective view of the processor cabinet to the endoscopic system shown in FIG. 1, with the top cover of the processor cabinet being removed and the front wall being cut away to better illustrate details of the illumination apparatus of the present invention.
Figure 3B:
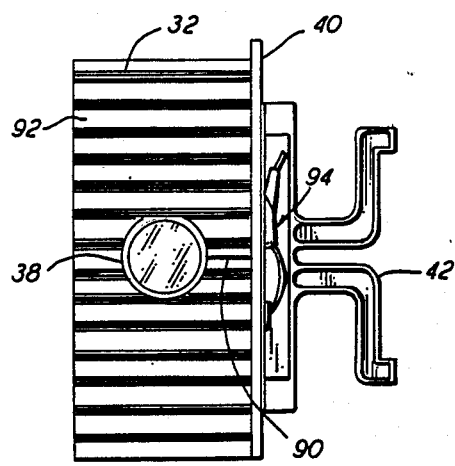
FIG. 3b is an enlarged side elevation view of the lamp assembly of the present invention.

An enlarged top perspective view of a processor cabinet 24 of video processor 16 is shown in FIG. 2. In FIG. 2, the top cover (not shown) of processor cabinet 24 has been removed and the front wall of cabinet 24 has been cut away to illustrate certain details of the preferred embodiment of an illumination apparatus 26. Illumination apparatus 26 comprises a lamp assembly 28 and a housing 30. Lamp assembly 28, as shown in FIGS. 2 and 3, has a first heat sink 32 and a second heat sink 34, which are positioned in a back-to-back arrangement such that a back wall 33 of heat sink 32 faces a back wall 35 of heat sink 34. Heat sinks 32,34 are supported together in a single assembly by a cover 36. In the preferred embodiment, cover 36 of lamp assembly 28 has an end edge 40 that extends beyond the side edges of heat sinks 32 and 34. Lamp assembly 28 further comprises a handle 42 mounted to cover 36. Heat sink 32 is substantially similar to heat sink 34, except for a lamp aperture 38 defined therethrough as shown in FIGS. 2 and 3b. A more detailed description of lamp assembly 28 will be described hereinbelow with reference to FIGS. 3 and 4.

In the preferred embodiment, housing 30 has at least a front wall 44 and a rear wall 46. Housing 30 is mounted to the bottom portion of cabinet 24. Housing 30 defines an insertion opening 48 configured and dimensioned to allow the insertion of lamp assembly 28 therein, as illustrated in FIG. 2. A rectangular-shaped notch 50 is contained in rear wall 46. Extended end edge 40 of lamp assembly 28 is configured and dimensioned to overlap opening 48 unless lamp assembly 28 is properly positioned such that extended end edge 40 is in alignment with rectangular-shape notch 50. Therefore, extended end edge 40 limits the insertion of lamp assembly 28 into opening 48.

As illustrated in FIG. 2, housing 30 may contain a side wall 52 containing a line-of-sight aperture 54. Line-of-sight aperture 54 is located in sidewall 52 such that optical alignment may be achieved with lamp aperture 38.

Figure 5:
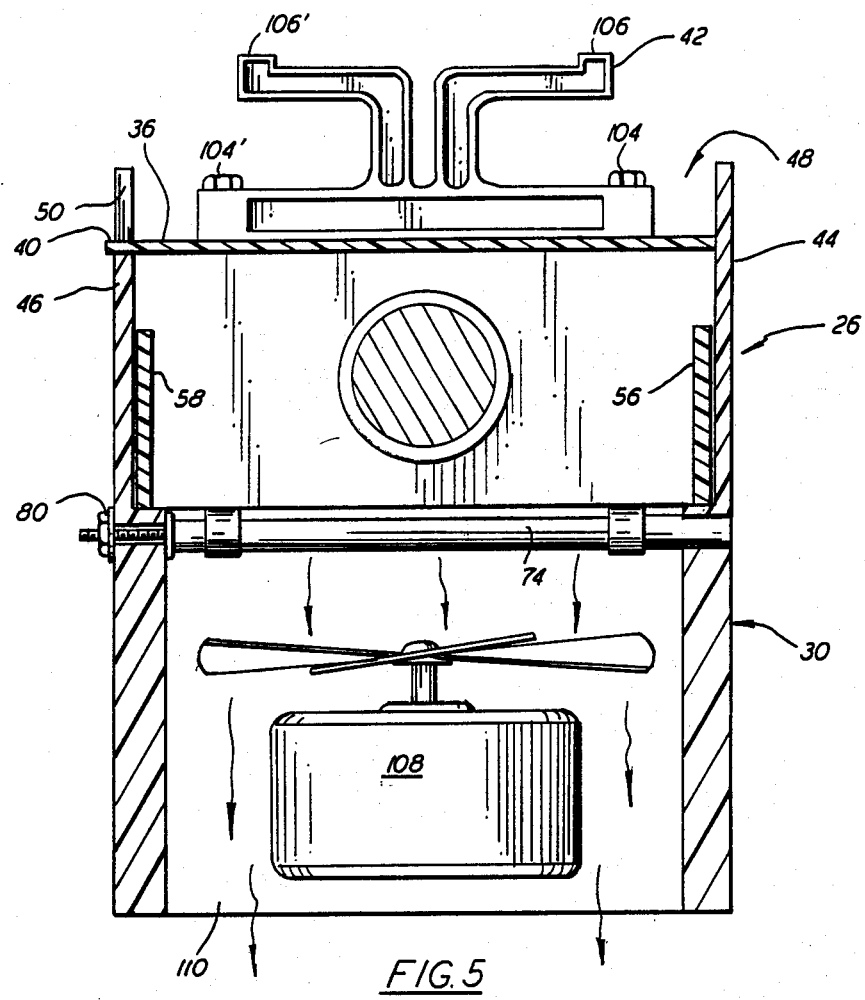
FIG. 5 is an enlarged sectional view of the illumination apparatus of the present invention, illustrating details of the lamp assembly inserted in the housing.

Housing 30 further comprises a pair of optical alignment ribs 56 and 58, as shown in FIGS. 2 and 5. Alignment rib 56 projects internally from the inside surface of front wall 44, as clearly shown in FIG. 5. Alignment rib 58 projects internally from the inside surface of rear wall 46, as clearly shown in FIGS. 2 and 5. Alignment ribs 56 and 58 are positioned, configured and dimensioned to slidably engage back walls 33 and 35 of heat sinks 32 and 34, to ensure optical alignment of lamp aperture 38 and line-of-sight aperture 54 when lamp assembly 28 is inserted into housing 30.

Figure 4A:
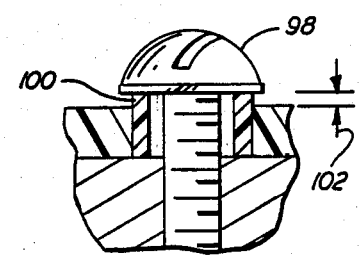
FIG. 4a is an enlarged fragmentary view of a slidable mounting arrangement, of one heat sink, constructed according to the present invention.
Figure 4:
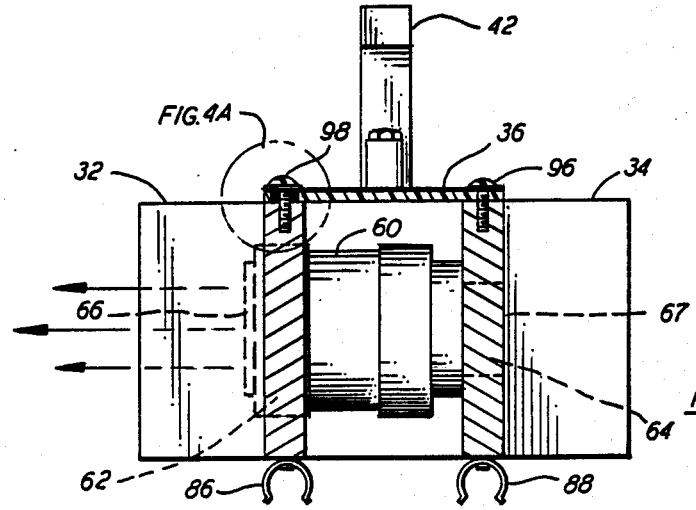
FIG. 4 is an enlarged horizontal sectional view through the lamp assembly taken substantially on line 4—4 of FIG. 3c.

Located at the core of illumination apparatus 26 is lamp or light source 60, as shown in FIG. 4. Lamp 60 contains at least two electrodes, a cathode 62 and an anode 64. In addition, lamp 60 contains a light emitting window 66, as shown in FIG. 4. Light source 60 may be a conventional flash lamp, sometimes referred to as an arc discharge lamp, comprising a Quartz envelope filled with an inert gas such as xenon. When the lamp is triggered, it produces a high intensity flash of white light.

Illumination apparatus 26 is optically coupled to viewing probe 18 through optical path 68, as shown in FIG. 2. Light emitted from light source 60, through light emitting window 66, lamp aperture 38, and line-of-sight aperture 54, passes outside housing 30, as shown in FIG. 2. Some video processors may employ a color filter wheel 70 for generating field sequential color images. Such a system is described in U.S. Pat. No. 4,523,224 to Longacre, Jr. As shown in FIG. 2, color filter wheel 70 is positioned to filter the light emitted from lamp 60.

Optical path 68 is further defined by a light deflection element 72, such as a mirror. From light deflection element 72, the light path of the light emitted from lamp 60, is directed to interface module 20, and out through viewing probe 18.

As illustrated in FIGS. 2 and 5, the preferred embodiment includes an electrical receptacle defined by a pair of electrical conductor rods 74 and 76. Electrical conductor rod 76 is fixedly mounted to the rear wall at one end and fixedly mounted to the front wall at the other end. Electrical conductor rod 74 is slidably mounted to rear wall 46 at one end and slidably mounted to front wall 44 at the other end, such that their relative positions are displaceable. A pair of elongated openings 78,78' are positioned, configured and dimensioned to receive the ends of conductor rod 74 and enable conductor rod 74 to be displaced along a line perpendicular to the axial dimension of conductor rod 74. One end of conductor rod 74 and one end of conductor rod 76 protrude through and out the rear wall 46 of housing 30, and function as a pair of power supply terminals 80,80', as shown, in part, in FIG. 5. Connected to power supply terminals 80,80' are power supply cables 82, as shown in FIG. 2. Cables 82 are routed directly to a power supply, not shown.

Figure 3C:
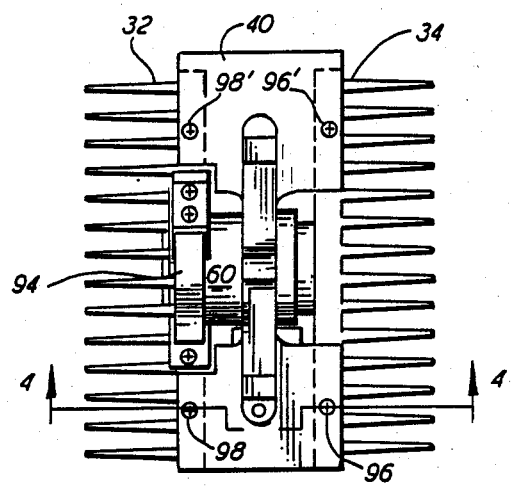
FIG. 3c is an enlarged top plan view of the lamp assembly of the present invention.
Figure 3A:
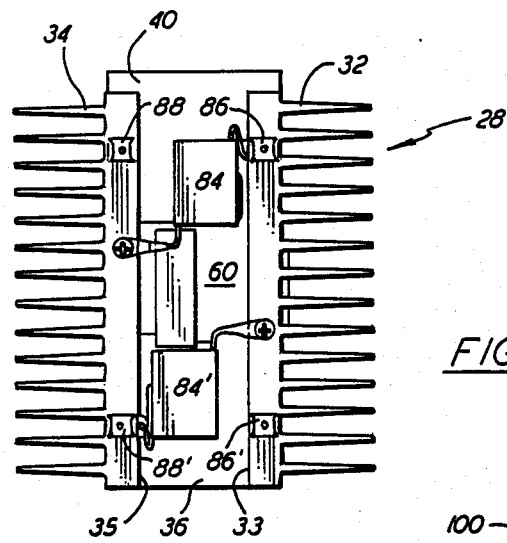
FIG. 3a is an enlarged bottom plan view of the lamp assembly of the present invention.

Referring to FIGS. 3 and 4, the preferred embodiment of lamp assembly 28 is shown in detail, in accordance with the present invention. An enlarged bottom plan view of lamp assembly 28 is shown in FIG. 3a. Heat sinks 32 and 34 are shown mounted to cover 36, having their respective back walls, 33,35 in opposing spaced relation to each other. Heat sinks 32 and 34 may each be constructed of a single extruded piece of aluminum.

Heat sinks 32 and 34 are thermally coupled to light source 60 and operate to dispose of heat energy generated by light source 60. Heat sinks 32 and 34 serve an additional function of operating as extensions to the electrodes of light source 60. Heat sinks 32 and 34 are electrically conducting and electrically coupled to cathode 62 and anode 64 respectively of light source 60.

Lamp assembly 28, in the preferred embodiment, further includes a pair of metallic resilient clips 86,86' mounted by fasteners to heat sink 32, and a pair of metallic resilient clips 88,88' mounted by fasteners to heat sink 34. Resilient clip pairs 86,86' and 88,88', are positioned, configured and dimensioned to resiliently embrace conductor rods 74 and 76 respectively, as partly shown in FIG. 5.

Cover 36 is constructed of an insulating material, such as a phenolic resin material. In addition to providing support for heat sinks 32,34, cover 36 acts as an electrical insulator between heat sink 32 and 34.

Also shown in FIG. 3a is a pair of shunting capacitors 84,84', each electrically connected to heat sink 32 at one terminal and electrically connected to heat sink 34 at the other terminal. The purpose of shunting capacitors 84,84' will be described in detail hereinbelow.

Referring to FIG. 3b, an enlarged side elevation view of lamp assembly 28, constructed in accordance with the present invention, is illustrated. As shown, heat sink 32 contains lamp aperture 38 therethrough to allow an unobstructed path for light emitted from lamp 60. Heat sink 32 contains a slit 90 running from its front wall 92 to its back wall 33 in one dimension, and from the perimeter of aperture 38 to its top edge, adjacent to cover 36, in the other dimension. The function of slit 90 is to provide incremental enlargement of aperture 38 to permit insertion of the front portion of lamp 60 therein, as shown in FIG. 4.

Figure 6:
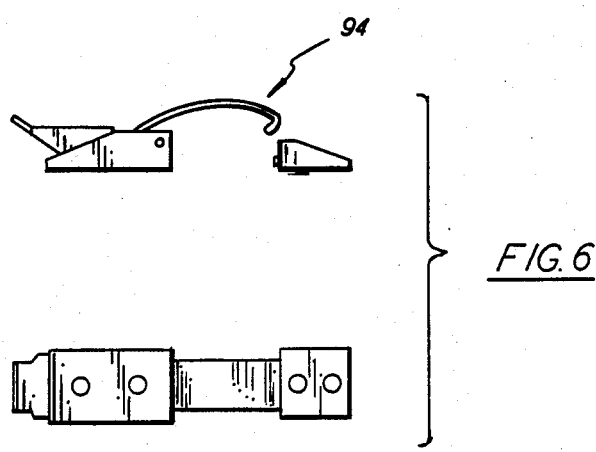
FIG. 6 illustrates enlarged side elevation and bottom plan views of the keeper and latch mechanism shown in FIG. 3 mounted and engaged on the lamp assembly.

A keeper and latch 94 is mounted by fasteners directly to heat sink 32, as shown in FIGS. 3b, and 3c. Keeper and latch 94 is employed to close slit 90, causing aperture 38 to constrict slightly. Accordingly, the front part of lamp 60 may be inserted through aperture 38 when keeper and latch 94 is open, as shown in FIG. 6, and be securely embraced by heat sink 32 when keeper and latch 94 is closed. Although heat sink 32 securely embraces the front part of lamp 60, including cathode 62, it is free to slide in the axial direction of lamp 60, over the front part of lamp 60. Notwithstanding the slidable engagement of heat sink 32 with the front part of lamp 60, electrical contact is maintained between heat sink 32 and cathode 62. A silicone compound coating may be applied around cathode 62 of lamp 60 to fill in air gaps between heat sink 32 and cathode 62 to improve the thermal conductivity between cathode 62 and heat sink 32. Heat sink 34 is fixedly mounted to a back end 67 of light source 60 by screws or other fasteners.

Referring to FIG. 4, a horizontal sectional view through lamp assembly 28 taken substantially on line 4—4, of FIG. 3c is shown. As illustrated in FIGS. 3c and 4, cover 36 is fixedly mounted to heat sink 34 by a pair of mounting screws 96,96', and loosely mounted to heat sink 32 by a pair of mounting screws 98,98'.

The loose mounting arrangement between heat sink 32 and cover 36 is achieved by boring a hole through cover 36 and inserting a bushing 100 therethrough, as illustrated in FIG. 4a. Bushing 100 may be dimensioned to closely fit within the bore. Mounting screw 98 is then inserted through bushing 100 and securely threaded into heat sink 32. The outside diameter of the shank of mounting screw 98 is smaller than the inside diameter of bushing 100; thus, heat sink 32 is permitted to float an incremental distance in a multiplicity of directions.

Mounting screw 98 is not fastened tightly against the surface of cover 36. The head of mounting screw 98, is suspended by a portion of bushing 100 protruding from the surface of cover 36. A space 102 is shown in FIG. 4a which is defined by the surface of cover 36 and the bottom face of the head of mounting screw 98. The same mounting arrangement is employed for mounting screw 98'.

Therefore, the combination of the slidable engagement of heat sink 32 with lamp 60, the loose mounting arrangement of cover 36 to heat sink 32, and the displaceable conductor rod 74 mounted in housing 30, provides lamp 60 with a support and electrical installation that is flexible and self-adjusting under a thermal load. Thus, damaging physical stresses imposed by thermal expansion and contraction of the heat sinks is minimized.

Referring to FIG. 5, an enlarged sectional view of the illumination apparatus of the present invention is illustrated showing details of lamp assembly 28 inserted in housing 30. Handle 42 is mounted to cover 36 by fasteners 104,104'. In the preferred embodiment, handle 42 is constructed of material that is a poor thermal conductor, such as phenylene oxide material. Therefore, lamp assembly 28 can be manually removed from housing 30 without the delay usually encountered in waiting for the lamp assembly to cool down. Handle 42 provides the additional function of acting as a support to retain lamp assembly 28 in the position shown in FIG. 5. This additional function is accomplished when the cover (not shown) of processor cabinet 24 is installed. The inside surface of the cover of cabinet 24 contacts handle 42 at a pair of upward projecting edge members 106,106', as shown in FIG. 5. Therefore, handle 42 is urged downward once the cover of cabinet 24 is installed, causing lamp assembly 28 to be retained in the position shown in FIG. 5.

A fan unit 108 is disposed within housing 30, and operates to exhaust air from housing 30 out a bottom opening 110. The exhausted air is passed through a vent contained in the bottom portion of cabinet 24 (not shown).

Housing 30 is constructed of a material, such as a phenolic resin material, that acts as an electrical insulator and a heat barrier. Housing 30 operates to electrically insulate the lamp assembly and electrical installation from other components located within processor cabinet 24. In addition, the heat generated by lamp assembly 28 is localized within the housing until exhausted by fan unit 108.

In addition to its physical support function, illumination apparatus 26 is configured to provde the electrical power supply circuit required to actuate lamp 60. The power supply circuit is defined between an electrical power supply (not shown) and lamp 60. The power supply circuit can be described as beginning with power supply cables 82 connected to a power supply at one end and connected to electrical conductors 74,76 at the other end, as partly shown in FIG. 2. Electrical conductors 74 and 76 are electrically coupled to heat sinks 32 and 34 respectively upon engagement of resilient clips 86,86' and 88,88' to electrical conductors 74 and 76 respectively. Heat sinks 32 and 34 are electrically conducting elements and insulated from each other by cover 36. Heat sink 32 is electrically coupled to cathode 62 of lamp 60. Heat sink 34 is electrically coupled to anode 62 of lamp 60. Therefore, an electrical circuit is created between a power supply (not shown) and lamp 60, configured to actuate lamp 60 upon application of the power supply to cables 82.

Shunting capacitors 84,84' connected across heat sink 32 and 34, as shown in FIG. 3a and described above, operate to short circuit or filter out unwanted electromagnetic oscillations generated in lamp 60. These oscillations can cause electromagnetic interference with other processor components. Therefore, the employment of capacitors 84,84', as described, substantially eliminates these problems.

While this invention has been explained with reference to the structure disclosed herein, it is not confined to the details set forth and this application is intended to cover any modifications and changes as may come within the scope of the following claims.

What is claimed is:

1. A video system having, a video processor mounted to a frame; a viewing probe coupled to the video processor that has an imaging device at its distal end; and an illumination apparatus coupled to the viewing probe; said illumination apparatus including:
   a lamp assembly containing, a light source having first and second electrodes for illuminating a target in the viewing range of the imaging device of the viewing probe, and heat disposing means, thermally coupled to said light source for disposing heat energy generated by said light source, said heat disposing means being arranged to support said light source,
   said heat disposing means having first and second heat sink members, each of said members being electrically conducting and one being electrically insulated from the other, said first and said second heat sink members being electrically coupled to the first and the second electrodes respectively of said light source;
   housing means having front and rear walls and containing an opening configured and dimensioned to permit the insertion of said lamp assembly therein, for housing said lamp assembly;
   a receptacle disposed within and supported by said housing means having first and second electrical conductors;
   plug means connected to said first and said second heat sink members for detachably coupling said first and said second heat sink members to the first and the second conductors of said receptacle respectively upon the insertion of said lamp assembly into said housing means;
   whereby said light source is actuated upon application of a power supply to the first and the second electrical conductors of said receptacle.

2. A video system as recited in claim 1, wherein said lamp assembly further contains a handle connected to said heat disposing means for enabling the manual removal of said lamp assembly from said housing means.

3. A video system as recited in claim 1, wherein said illumination apparatus further comprises means on said heat disposing means and extending therefrom to overlap the opening of said housing means for limiting the axial insertion of said lamp assembly into the opening of said housing.

4. A video system as recited in claim 1 wherein said plug means comprises resilient clips configured and dimensioned to resiliently embrace the first and the second conductors of said receptacle.

5. A video system as recited in claim 1, wherein said heat disposing means further comprises an insulating member, disposed between said first and said second heat sink members, for physically supporting said first and said second heat sink members, said first heat sink member being loosely mounted to said insulating member and said second heat sink member being fixedly mounted to said insulating member.

6. A video system as recited in claim 1, wherein said lamp assembly further comprises shunting means, electrically connected across said first and said second heat sink members, for shunting to an electrical ground electrical power signals operating in a predetermined undesired frequency range.

7. A video system as recited in claim 1, wherein one of said heat sink members contains a lamp aperture to permit the projection of light energy from said source to a point external to said lamp assembly.

8. A video system as recited in claim 7, wherein at least one of said heat sink members is slidably mounted to its respectively coupled electrode of said light source.

9. A video system as recited in claim 8, wherein at least one of said electrical conductors is slidably mounted in said housing means such that the relative positions of said first and said second electrical conductors are displaceable.

10. A video system as recited in claim 9, wherein said lamp assembly further contains a handle connected to said heat disposing means for enabling the manual removal of said lamp assembly from said housing means.

11. A video system as recited in claim 9. wherein said illumination apparatus further comprises means on said heat disposing means and extending therefrom to overlap the opening of said housing means for limiting the axial insertion of said lamp assembly into the opening of said housing.

12. A video system as recited in claim 9 wherein said plug means comprises resilient clips configured and dimensioned to resiliently embrace the first and the second conductors of said receptacle.

13. A video system as recited in claim 9, wherein said heat disposing means further comprises an insulating member, disposed between said first and said second heat sink members, for physically supporting said first and said second heat sink members, said first heat sink member being loosely mounted to said insulating member and said second heat sink member being fixedly mounted to said insulating member.

14. A video system as recited in claim 9, wherein said lamp assembly further comprises shunting means, electrically connected across said first and said second heat sink members, for shunting to an electrical ground electrical power signals operating in a predetermined undesired frequency range.

* * * * *